United States Patent
Pitesky

[11] Patent Number: 6,045,499
[45] Date of Patent: Apr. 4, 2000

[54] TONGUE RETRACTOR

[76] Inventor: Isadore Pitesky, 4001 Linden Ave., Long Beach, Calif. 90807

[21] Appl. No.: 09/320,991

[22] Filed: May 26, 1999

Related U.S. Application Data

[63] Continuation-in-part of application No. 09/181,692, Oct. 27, 1998, abandoned.

[51] Int. Cl.[7] .................................................. A61B 13/00
[52] U.S. Cl. ........................................... 600/240; 600/241
[58] Field of Search ................................... 600/239, 240, 600/241

[56] References Cited

U.S. PATENT DOCUMENTS

| | | |
|---|---|---|
| D. 28,973 | 7/1898 | Sawyer . |
| D. 52,766 | 12/1918 | Jacoby . |
| D. 212,453 | 10/1968 | Wallace . |
| D. 224,173 | 7/1972 | Clifford . |
| D. 329,287 | 9/1992 | Ziese . |
| D. 359,556 | 6/1995 | Hale et al. . |
| 412,409 | 10/1889 | Osborne . |
| 1,388,170 | 8/1921 | Cameron . |
| 1,396,933 | 11/1921 | Jacoby . |
| 2,697,432 | 12/1954 | Scinta ...................................... 600/239 |
| 2,723,661 | 11/1955 | Hull . |
| 3,154,069 | 10/1964 | Ring . |
| 3,162,191 | 12/1964 | Canan . |
| 3,315,664 | 4/1967 | Hill . |
| 5,518,503 | 5/1996 | Rooney et al. . |
| 5,656,014 | 8/1997 | Ronney et al. . |
| 5,697,890 | 12/1997 | Kolfenbach et al. ................... 600/240 |

*Primary Examiner*—Paul J. Hirsch
*Attorney, Agent, or Firm*—Fulwider Patton Lee & Utecht, LLP

[57] ABSTRACT

A disposable tongue retractor having a tapered elongated body with downwardly curving hook ends.

16 Claims, 3 Drawing Sheets

TONGUE RETRACTOR

This application is a continuation-in-part of U.S. Ser. No. 09/181,692 filed Oct. 27, 1998.

BACKGROUND OF THE INVENTION

1. Field of the Invention

The invention relates to the field of medical equipment and more particularly to disposable tongue retractors.

2. Description of the Prior Art

It has long been the practice of medical doctors, in the examination of a patient, to examine the patient's throat to determine, for example, if the throat is inflamed or the tonsils enlarged or infected. This requires swabbing for bacterial culture, a procedure detested by both child and adult patients. The long accepted procedure has been for the physician to insert a straight flat stick, commonly referred to as a tongue depressor, into the mouth along a downwardly and rearwardly inclined plane to press downwardly on the back of the tongue to lower the tongue and enlarge the opening in the throat so as to view the surface tissue of the throat itself. Unfortunately, this procedure frequently causes intense gagging.

Commonly known disposable tongue depressors come in different sizes for adults and children and are usually fabricated from flat strips of wood a little over 1 cm wide, about 11 cm long and rounded at their opposite ends. These depressors have long been a standard in the industry and have experienced little improvement over the years.

Efforts to improve on these flat veneer sticks have led to the proposal that the sticks themselves be subjected to an extremely expensive procedure where the wood is moistened and heated to be formed to a desired configuration. It was believed that there would be a benefit to providing a lateral offset between the hand grip portion and the tongue depressing portion. A device of this type is shown in U.S. Pat. No. 2,723,661 to Hull. While effective for providing the desired offset between the handle portion and tongue depressing portion, such a device is expensive to manufacture and does little to facilitate drawing of the tongue forward without undue downwardly depression of the tongue itself.

There would be a benefit in providing a device which would allow the physician to draw the tongue forwardly rather than just pushing it downwardly. In this regard, it has been proposed to provide a tongue depressor which incorporates a gradual continuous curve from the forward to the rearward end thereof and is formed on at least its bottom side with serrations which might actually engage the tongue to provide a frictional force between the tongue depressor and the tongue in effort to provide a means for drawing the tongue forward. A device of this type is shown in U.S. Pat. No. 5,518,503 to Rooney. While offering some benefit, the device proposed by Rooney suffers the shortcoming that the curvature of the longitudinal distance of the depressor is inadequate to allow the physician to positively engage behind the tongue of the patient to positively draw the tongue forwardly without undue downward pressure on the tongue itself.

Further efforts have led to the proposal of a rather elaborate tongue depressor including a handle portion constructed with an illuminating light and having a tongue engaging portion which is curved slightly downwardly and formed on its underside with sawtooth serrations defining teeth intended to grippingly engage the tongue in hopes that such gripping action would facilitate in forward drawing of the tongue. A device of this type is shown in U.S. Pat. No. 5,656,014 to Rooney. Such devices, while serving to provide some illumination, are expensive to manufacture and the sawtooth-like serrations can introduce some discomfort for the patient, particularly one with a sore tongue.

Other efforts have led to combine a metal tongue depressor with a mirror examination instruments. The ends of the tongue depressor are bent downwardly at an angle so that a flat planar mirror segment may be mounted therein. A device of this type is shown in U.S. Pat. No. 3,162,191 to Canan. Such devices have little utility for effectively drawing the tongue forward without extensive downward depression and are relatively expensive to manufacture, are not disposable and are difficult to sterilize.

Other work led to the proposal of an insufflator having a tubular dispenser and polished metal retractor paddle to engage over and behind the tongue to drive it down for viewing the throat to guide the medical doctor in using the insufflator tube. A device of this type is shown in U.S. Pat. No. 412,409 to Osborne. Such devices do not lend themselves to general throat examination and are so expensive to manufacture, they are not typically thought of as being disposable. Many of these prior art devices are intended to be used with local or general anesthesia during surgery.

Consequently, there exists a need for an inexpensive tongue retractor which will effectively engage behind the patient's posterior tongue in such a manner that the posterior tongue can be drawn forwardly without undue downward pressure thereon. The device must be of relatively inexpensive construction, disposable and the same instrument should be adaptable for both child and adult patients.

SUMMARY OF THE INVENTION

The present invention is a disposable tongue retractor characterized by an elongated plastic body formed on at least one end with a downwardly curving hook to engage behind the posterior tongue so that it can be drawn forward without undue downward pressure. In the preferred embodiment, the retractor is curved in transverse cross section to enhance rigidity and is concaved downwardly to form a shallow, semi-circular, upwardly opening trough designed for nesting therein of a penlight to illuminate the patient's throat. The invention is an improvement over the prior art in that it does not require the physician to press down on the patient's tongue, thus eliminating the tendency to produce the attendant gag reflex. Rather, the invention is designed to engage and pull the patient's posterior tongue forward without undue downward pressure on the posterior tongue. Further, the invention allows for a light source such as a pen light to be positioned on the tongue retractor such that both light and retractor can be held in one hand, thereby allowing the physician's free hand to be used to take a throat culture or swab the throat.

In one embodiment, the device incorporates a reinforcing rib on such hook to support it against flexing or straightening when longitudinal forces are applied thereto.

Other features and advantages of the invention will become apparent from the following detailed description, taken in conjunction with the accompanying drawings, which illustrate by way of example, the features of the invention.

DETAILED DESCRIPTION OF THE PREFERRED EMBODIMENT

Figure 1:
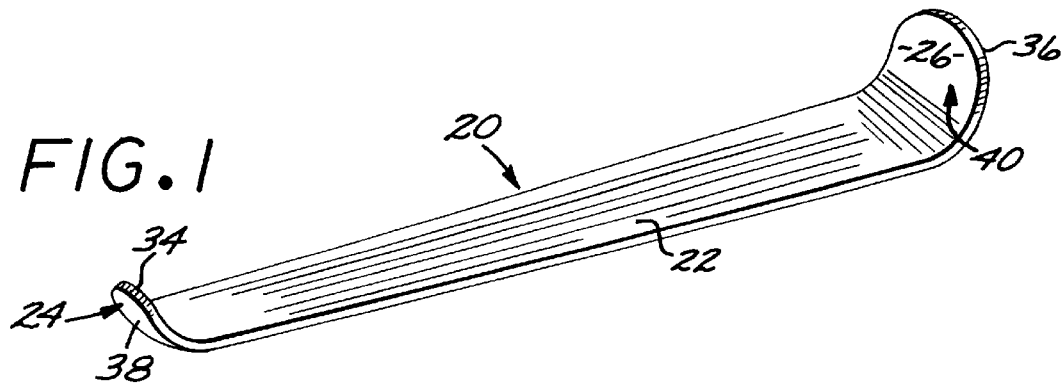
FIG. 1 is a bottom perspective view of a disposable tongue retractor embodying the present invention.
Figure 2:
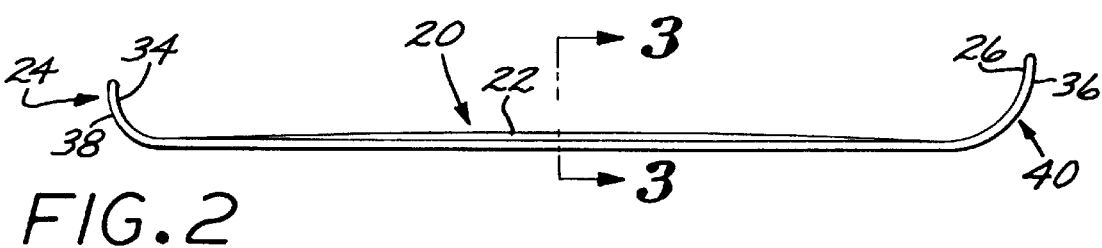
FIG. 2 is a side view of the tongue retractor shown in FIG. 1.
Figure 3:
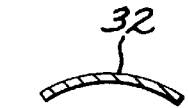
FIG. 3 is a cross sectional view taken along line 3—3 of FIG. 2.

Disposable tongue depressors are in common use throughout the world. Thousands of tongue depressors are used each day and are disposed after a single use. In even the most common examination of a patient, a physician usually endeavors to gain access to the patient's throat to examine the throat tissue and look for various signs. With emphasis on efficiency in the medical industry, a certain priority is placed on the necessity of such disposable devices being economical to manufacture. Doctors and patients alike have known for many years that throat examinations produce considerable discomfort to many such patients typically producing a gagging reaction to the depression of the tongue. Consequently, physicians are sometimes tempted to move rapidly through the throat examination exercise so as to minimize patient discomfort. This, and the general ineffectiveness of commonly used planar tongue depressors, often results in a physician failing to gain a high quality visual examination of the patient's throat. Consequently, there exists a need for a tongue retractor which will be effective to engage positively behind the posterior tongue so that the tongue can be essentially drawn forward rather than being depressed downwardly so as to minimize the discomfort and maximize the procedure for opening the oropharynx for a high quality examination. The tongue depressor of the present invention solves this need.

The tongue depressor, generally designated 20, of the present invention may be constructed of metal, plastic or other relatively rigid material and includes an elongated generally planar shank 22 and is curved downwardly on its opposite ends to form respective large and small hooks 40 and 24. In the preferred embodiment, the hooks are configured with a generally circular shape and the large hook is configured with a radius of curvature of about 20 mm and the small hook 24 configured with a radius of curvature of 10 mm to project downwardly respective distances of about 20 mm and 15 mm from the longitudinal plane of the shank 22. This then provides relatively small radii of curvature to complement the anatomy of the pharynx of respective adult and child so that the working end of the tongue retractor may be inserted in the patient's mouth (FIG. 5) to hook the hook behind the posterior tongue so that a forward motion will draw the tongue forwardly in the mouth and move the tongue forwardly. Then, as long as the patient maintains his or her mouth open, the examining physician will have a wide unobstructed view through the patient's mouth above the tongue retractor and into the critical throat area.

The retractor is somewhat wedge shaped in plan view so its opposite edges taper from a shank width of about 18 mm at the body of the hook 40 to a width of about 15 mm at the hook 24.

The tongue depressor is formed so that the terminal ends of the respective hooks 24 and 40 with what, in the respective working positions constitute forwardly facing paddles 34 and 36, engage behind the tongue of the patient.

Figure 4:
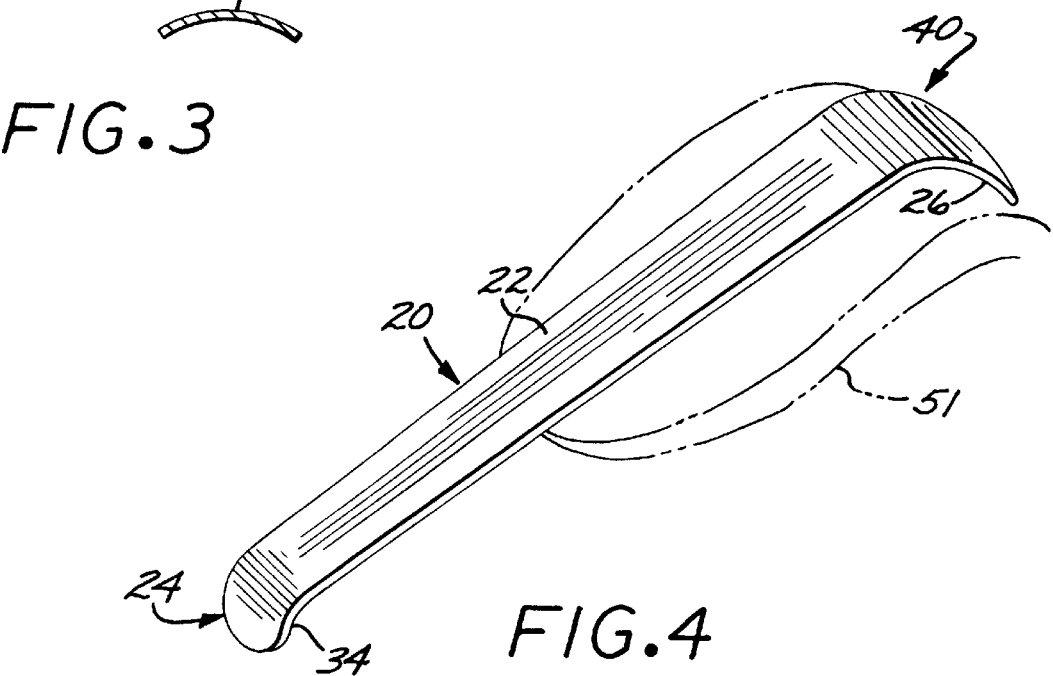
FIG. 4 is a top perspective view of the retractor shown in FIG. 1 depicted in place on a tongue.

While not critical to the invention, in the preferred embodiment, the shank 22 is, as viewed in FIG. 4, curved centrally downwardly in concave fashion to form an upwardly opening concave trough 44 to thereby provide enhanced structural rigidity to the tongue retractor throughout the length thereof and to provide an upwardly opening elongated arcuate nest. Preferably such curvature extends over into the hooks 24 and 40 themselves so as to provide reinforcement against bending of the hooks as forces are applied thereto during the working manipulation thereof.

While the curvature of the respective hooks 24 and 40 might vary for various applications, I have discovered that the respective radii of curvature of 10 mm and 20 mm is ideal for child and adult applications. In the preferred embodiment, the hooks 24 and 40 are curved to form respective sectors of circles and project laterally from the plane of the shank to terminate in respective ends spaced about 15 mm and 20 mm, respectively, from the plane of such shank. The hook may vary from a shape which will provide a downwardly projecting tab, configured with a forwardly facing surface oriented at an angle of 90° and 80° to the shank so as to provide the required position behind the posterior tongue. It is only important that the hook for the particular application have sufficient lateral reach so that the respective forwarding facing load bearing surfaces of the respective paddles 26 and 34 extend sufficient far down the throat to have an extent behind the tongue while the shank remains fairly longitudinal, all without projecting so far down the throat as to induce a gag reflex.

It will further be appreciated that, while I selected the length of my tongue retractor at 12 cm for the preferred embodiment, it may take many different width and length configurations and may be constructed with a hook at only one end for one of different selected applications, such as infant, adolescent or adult.

Figure 5:
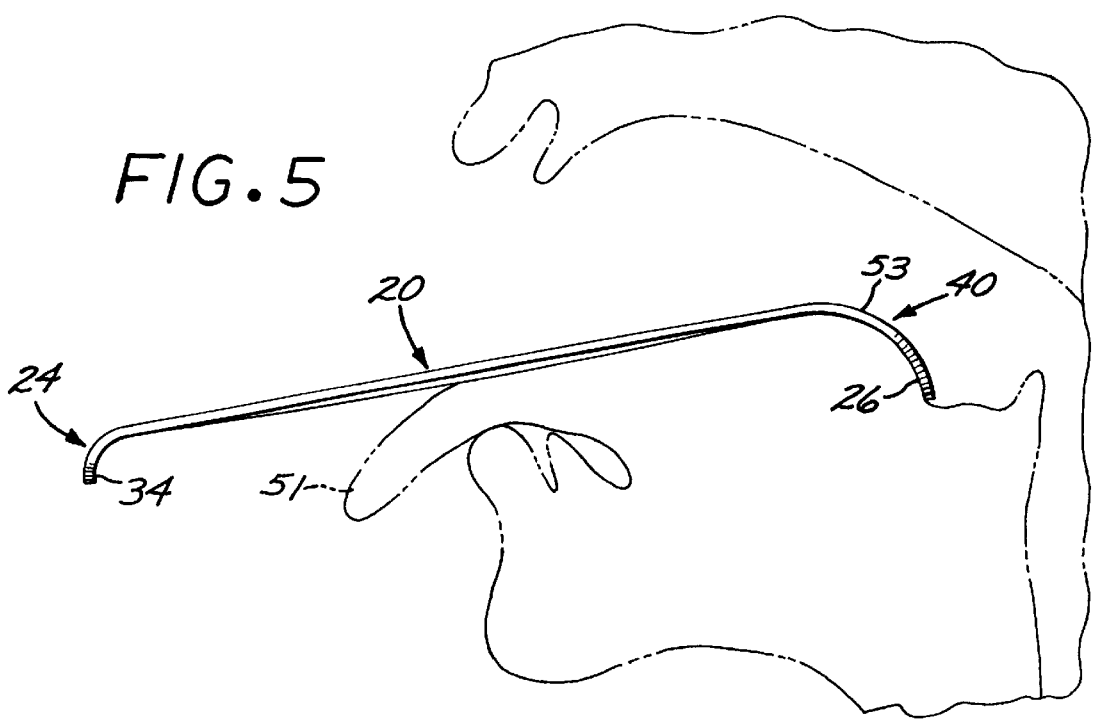
FIG. 5 is a side view, in enlarged scale, depicting the tongue retractor shown in FIG. 1 in place on a tongue and upper pharynx.

In operation, it will be appreciated that the tongue retractor of the present invention will typically be manufactured and then packaged in multiple units. When the physician desires to make an examination, he or she will remove one of the tongue retractors and ask the patient to open his or her mouth. Assuming the examination is to be of an adult patient as shown in FIG. 5, the patient will open his or her mouth and extend the tongue 53 to the position shown. The retractor 20 may then be inserted with the large hook 40 behind the posterior tongue 53. With the hook hooked downwardly behind the tongue 53, the physician may grasp the shank or place his or her thumb or finger behind the small hook 24 to utilize it as a handle for drawing forwardly while pushing down only gently on the shank to maintain gentle downward engagement on the upward surface of the tongue. The paddle 26 of the large hook 40 will then engage behind the tongue 53 to draw the tongue positively and gently forwardly without undue pressure downwardly on the back of the tongue. This then will allow the physician to have a relatively unobstructed view of the tissue in the throat area while the mouth is maintained open.

Figure 6:
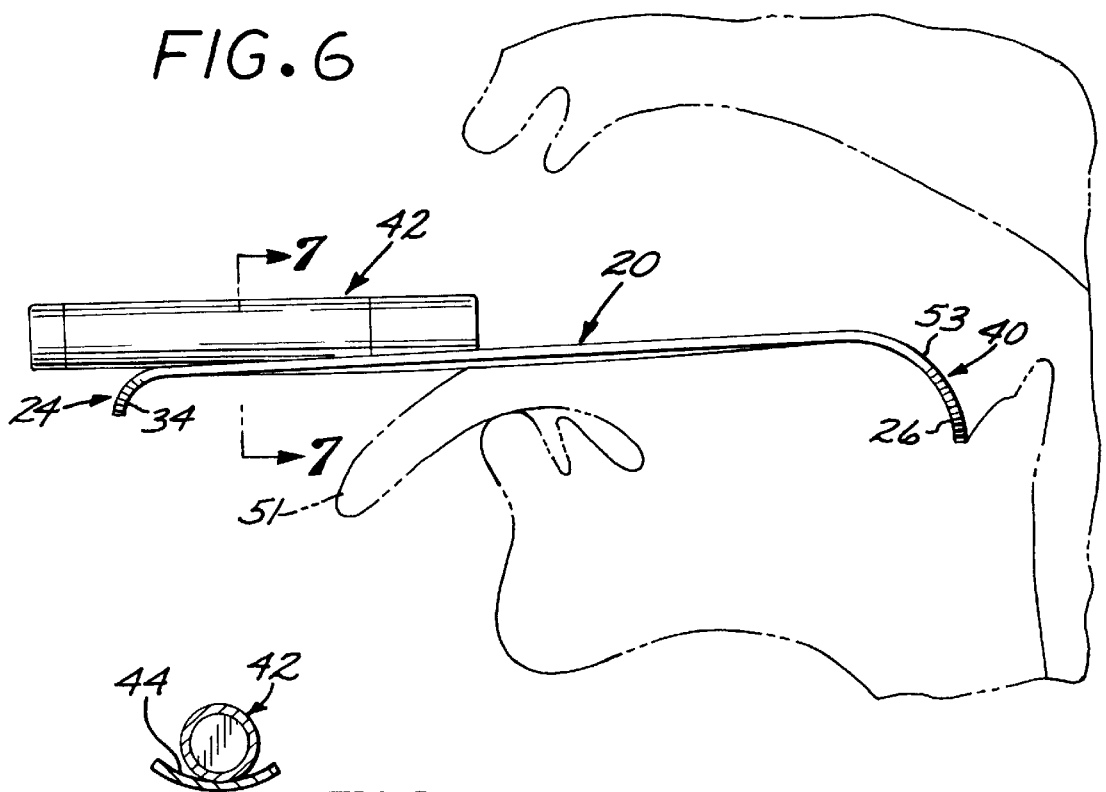
FIG. 6 is a view similar to FIG. 5 showing a pen light nested on the retractor.
Figure 7:
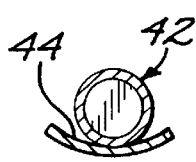
FIG. 7 is a cross sectional view taken along line 7—7 of FIG. 6.

Additionally, if desired, the physician can nest a pen light 42 in the concave nesting groove 44, shown in FIG. 6, and simultaneously grasp such pen light and the tongue retractor in one hand during the above described maneuver. The pen light will illuminate the throat as such pen light and retractor is held in one hand by the physician. The physician may then pick up a culture swab with the other hand and access the throat area to take a culture without the assistance of a head mirror, head light or other less convenient or readily available illuminating mechanisms.

On other occasions when the physician might want to examine a child, the same procedure may be repeated, except that the small hook 24 will be inserted in the child's throat for engagement behind the child's tongue and the physician can grasp the large hook end and draw forwardly on the hook 40 to draw the child patient's tongue forwardly.

Figure 8:
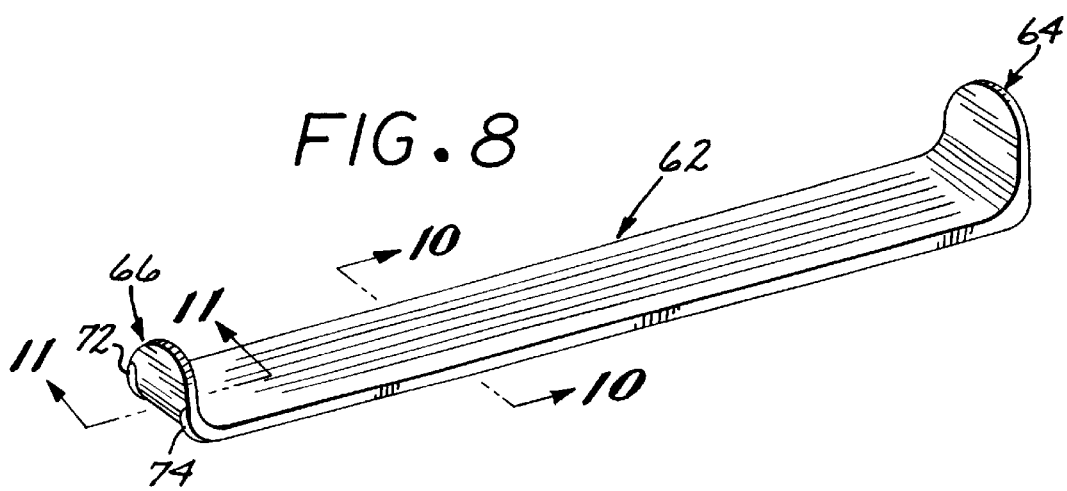
FIG. 8 is a perspective view of a second embodiment of the disposable tongue retractor of the present invention.
Figure 9:
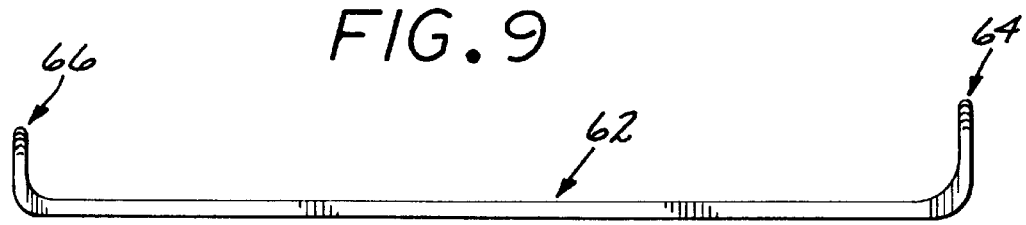
FIG. 9 is longitudinal front view thereof.
Figure 10:
FIG. 10 is a transverse sectional view, in enlarged scale, taken along the line 10—10 of FIG. 8.
Figure 11:
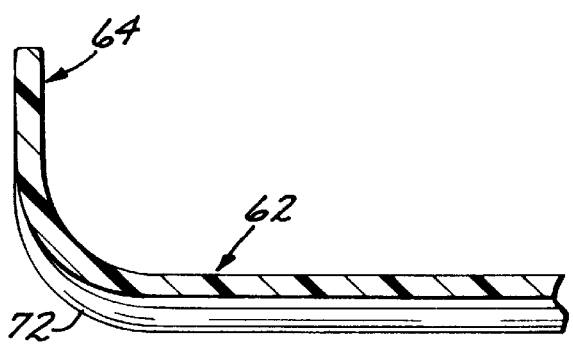
FIG. 11 is a partial longitudinal sectional view, in enlarged scale, taken along the line 11—11 of FIG. 8.

The embodiment of the disposable tongue retractor shown in FIG. 8 is similar to that shown in FIGS. 1–7. The retractor includes, generally, an elongated shank 62 curved transversely at its opposite ends to form respective large and small retractor hooks 64 and 66 projecting perpendicular to the plane of the shank. The shank 62 tapers from a width of 1.8 cm at its large end to 1.5 cm on its small end. The respective reinforcing ribs 72 and 74 are formed on the opposite sides of such shank and project from the respective curves defining the respective roots of the respective hooks 64 and 66 to thus reinforce the hooks against straightening thereof when longitudinal forces are applied to the shank and one or the other of such hooks are used to retract the tongue.

The retractor may be constructed of any acceptable type of plastic and, in the preferred embodiment, is constructed of relatively rigid plastic such as a polystyrene. The hook 64 projects laterally 1.8 cm from the face of the shank and the hook 66 1.0 cm from such face.

The shank 62 and hooks 64 and 66 are about 2 mm thick. The shank is formed on its opposite lateral edges with the reinforcing ribs 72 and 74 about 1.2 mm in cross section and projecting longitudinally at the opposite ends of the retractor to wrap around the respective roots of the respective hooks 64 and 66 to provide reinforcement against longitudinal flexing or flattening out of such hooks when longitudinal forces are applied thereto. It will be appreciated from the foregoing that such hooks may be used as either a retractor paddle to be placed behind the patient's tongue or may be used as a handle behind which the physician may hook his or her finger to provide for purchase to draw the retractor forwardly for drawing of the tongue forwardly.

It will be appreciated that with the plastic construction of the retractor of the present invention, it is relatively inexpensive to manufacture so it can be conveniently utilized in typical everyday throat examinations performed by internists, general practitioners and other specialists all over the country. With the retractor of the present invention, the retractor can be stored in stacked relationship in compact packaging and, if desired, can be packaged in sterilized packaging. It can be utilized for routine throat examination and, because of its inexpensive nature, it is disposed of after each use, thus minimizing the expense to the patient or insurance carrier, an objective carrying great weight in today's economy.

It will be appreciated that a new and improved form of tongue retractor has been provided. While only the presently preferred embodiment has been described in detail, as will be apparent to those skilled in the art, certain changes and modifications can be made without departing from the scope of the invention as described by the following claims.

What is claimed is:

1. A disposable throat examination tongue retractor device for engaging a patient's tongue to draw it forwardly for reviewing of the throat and comprising:

an elongated generally rectangular plastic shank formed at its opposite ends with first and second laterally curved hooks having respective radii of curvatures of substantially 10 mm and 20 mm respectively, and being tapered along its opposite lateral edges from a width at said first end of substantially 13 mm to substantially 18 mm at said second end, said first curved hook being configured to project laterally of said shank substantially 10 mm and said second curved hook being configured to project laterally of said shank substantially 20 mm.

2. A disposable tongue retractor device as set forth in claim 1 wherein:

said shank is formed with a generally convex transverse cross section.

3. A disposable tongue retractor device as set forth in claim 1 wherein:

said shank is formed with a laterally opening trough for nesting therein of a pen light.

4. A disposable tongue retractor device as set forth in claim 1 wherein:

said first and second hooks project laterally in the same lateral direction from the plane of said shank.

5. A disposable tongue retractor device as set forth in claim 1 wherein:

said first and second hooks project laterally in opposite directions from the plane of said shank.

6. A disposable tongue retractor device as set forth in claim 1 wherein:

said shank is formed at its opposite sides with laterally projecting-reinforcing ribs.

7. A disposable tongue retractor device as set forth in claim 1 that includes:

at least one reinforcing rib on at least one of said hooks.

8. A disposable tongue retractor device as set forth in claim 1 that includes:

reinforcing ribs on the opposite sides of at least one of said hooks.

9. A disposable tongue retractor device as set forth in claim 1 that includes:

reinforcing ribs on the opposite sides of said hooks.

10. A disposable tongue retractor device as set forth in claim 1 wherein:

said shank is constructed of polystyrene.

11. A disposable throat examination tongue retractor device for engaging a patient's tongue to draw it forwardly for viewing of the throat and comprising:

an elongated plastic shank plate formed on one extremity with a laterally projecting retractor hook for engagement behind the patient's tongue and on its opposite extremity with a handle terminating in a laterally extending second hook; and a pair of reinforcing ribs projecting longitudinally on opposite edges of said shank plate and extending laterally onto opposite edges of at least one of said hooks to resist against flexing whereby a technician may grasp said handle and introduce said retractor device horizontally into said patient's mouth to engage said hook behind said tongue and draw said handle horizontally forwardly to draw said tongue forwardly for viewing of said throat.

12. A disposable tongue retractor as set forth in claim 11 wherein:

said reinforcing ribs extend laterally onto opposite edges of both hooks.

13. A disposable tongue retractor device as set forth in claim 11 wherein:

said shank includes a longitudinal plane; and at least one of said hooks projects perpendicularly from said longitudinal plane.

14. A disposable tongue retractor as set forth in claim 13 wherein:

both of said hooks project perpendicularly from said plane.

15. A disposable tongue retractor device as set forth in claim 11 wherein:

said retractor hook is formed to curve laterally from said shank.

16. A disposable throat examination tongue retractor device for engaging a patient's tongue to draw it forwardly for viewing of the throat and comprising:

an elongated generally plastic shank plate curved centrally downward in a concave fashion, forming an upwardly opening concave trough and formed at its first and second ends with respective first and second laterally curved hooks curved to project laterally of said shank substantially 10 mm and 20 mm, respectively.

* * * * *